(12) United States Patent
Casey

(10) Patent No.: US 11,844,381 B2
(45) Date of Patent: Dec. 19, 2023

(54) FOREARM SUPPORT PILLOW FOR USE WITH SHOULDER SLING

(71) Applicant: Michael Casey, Scottsdale, AZ (US)

(72) Inventor: Michael Casey, Scottsdale, AZ (US)

( * ) Notice: Subject to any disclaimer, the term of this patent is extended or adjusted under 35 U.S.C. 154(b) by 0 days.

(21) Appl. No.: 17/867,898

(22) Filed: Jul. 19, 2022

(65) Prior Publication Data

US 2023/0046130 A1 Feb. 16, 2023

Related U.S. Application Data

(60) Provisional application No. 63/231,991, filed on Aug. 11, 2021.

(51) Int. Cl.
| | |
|---|---|
| *A47G 23/02* | (2006.01) |
| *A47G 23/06* | (2006.01) |
| *A61F 5/37* | (2006.01) |
| *A41D 13/05* | (2006.01) |
| *A41D 27/20* | (2006.01) |

(52) U.S. Cl.
CPC ......... *A41D 13/0568* (2013.01); *A41D 27/20* (2013.01); *A61F 5/3738* (2013.01)

(58) Field of Classification Search
CPC .... A61F 5/3746; A61F 5/3753; A61F 5/3738; A41D 13/0568; A41D 27/20; A47G 23/0208; A47G 23/0216; A47G 23/0641
See application file for complete search history.

(56) References Cited

U.S. PATENT DOCUMENTS

| | | | |
|---|---|---|---|
| D449,206 S  * | 10/2001 | DuBow | D7/708.1 |
| 6,494,339 B1 * | 12/2002 | Engelhard | A47G 23/0225 220/DIG. 25 |
| D681,407 S  * | 5/2013 | Edwards | D7/708 |
| 9,051,082 B1 * | 6/2015 | Klinge | A47G 19/2205 |
| D963,435 S  * | 9/2022 | Wang | D7/701 |
| 2010/0263100 A1 * | 10/2010 | Clement | A47G 23/0225 2/66 |
| 2016/0278556 A1 * | 9/2016 | Almaguer | A47G 23/0208 |
| 2019/0159613 A1 * | 5/2019 | Longstaff | B65D 81/3876 |
| 2020/0054084 A1 * | 2/2020 | Kramer, IV | A61F 5/373 |
| 2021/0186238 A1 * | 6/2021 | Kilo | A47G 9/1045 |

FOREIGN PATENT DOCUMENTS

GB 2516811 A * 2/2016

OTHER PUBLICATIONS

DE 20 2021 110 279 U1, Christmann, Mar. 2021.*

* cited by examiner

*Primary Examiner* — Camtu T Nguyen
(74) *Attorney, Agent, or Firm* — Brown & Michaels, PC

(57) ABSTRACT

A forearm support which includes at least a first cutout on an end of the support that can adequately maintain a beverage container in an upright position such that liquid present in the beverage container does not spill or empty out of the container through a top opening during use of the forearm support by a wearer.

17 Claims, 3 Drawing Sheets

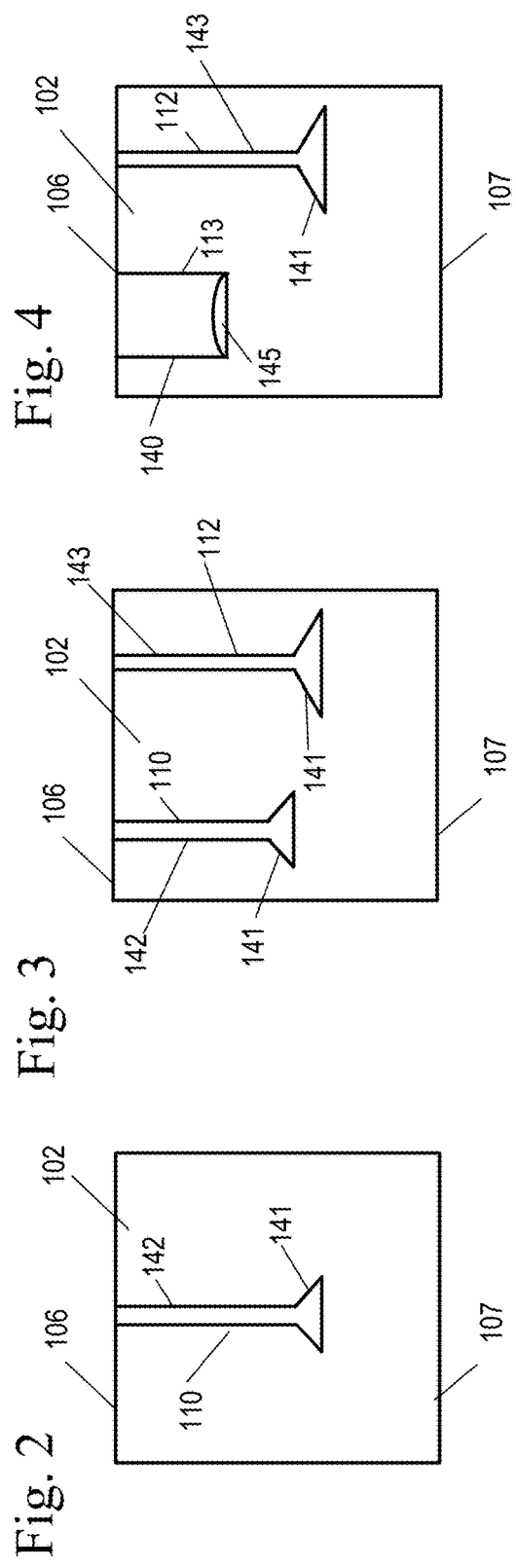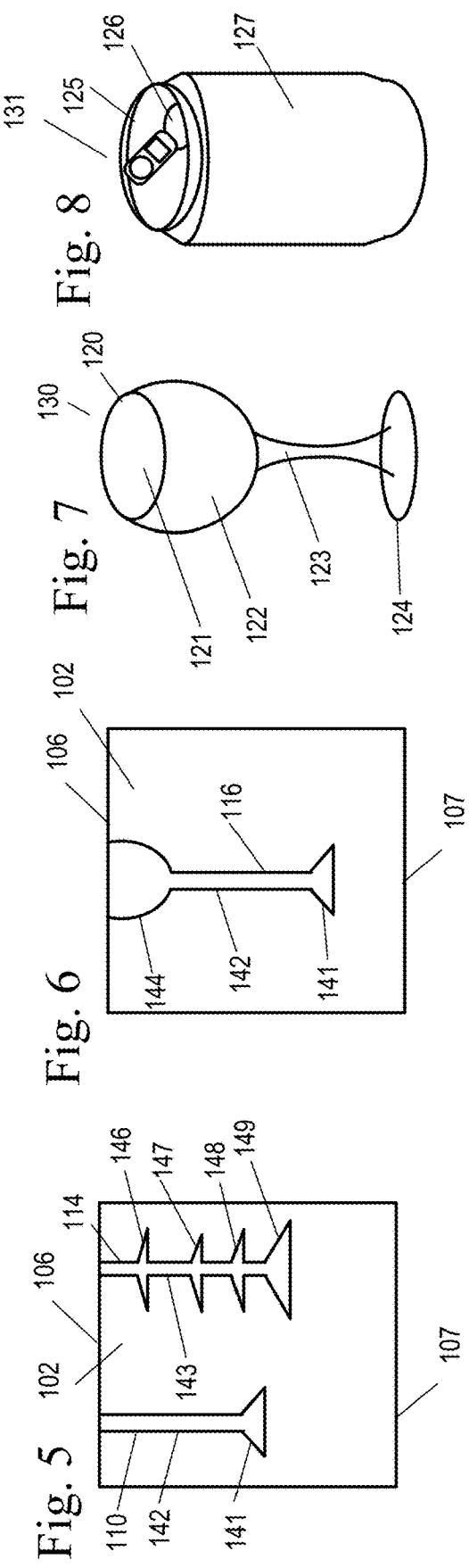

FOREARM SUPPORT PILLOW FOR USE WITH SHOULDER SLING

CROSS-REFERENCE TO RELATED APPLICATIONS

This application claims one or more inventions which were disclosed in Provisional Application No. 63/231,991, filed Aug. 11, 2021, entitled "FOREARM SUPPORT PILLOW FOR USE WITH SHOULDER SLING". The benefit under 35 USC § 119(e) of the United States provisional application is hereby claimed, and the aforementioned application is hereby incorporated herein by reference.

BACKGROUND

The present invention relates to an abduction pillow or forearm support for use with a shoulder sling, and more specifically to an abduction pillow or forearm support for holding beverages.

Physicians frequently treat many shoulder ailments with shoulder slings. For example, following a shoulder dislocation or shoulder surgery, a physician may place the patient's affected arm in a sling so that the shoulder remains motionless while it heals. Many simple slings comprise just a pouch that is supported by a strap around the wearer's neck. The shoulder can be further stabilized by adding a forearm support or abduction pillow that is a unitary block of synthetic foam material that supports a wearer's arm at a desired abduction angle. The forearm support is present between the wearer's waist and the forearm in the sling. The forearm support can be integrally connected to the sling or separate from the sling.

With a wearer's arm in a sling, and immobilized, movements and carrying of objects is significantly limited and can only be carried out using the remaining arm and hand. This can be cumbersome for the wearer when they need to carry a drink and other objects, especially in a social or professional setting.

SUMMARY

According to one embodiment of the present invention, a forearm support includes at least a first cutout that can adequately maintain a beverage container in an upright position such that liquid present in the beverage container does not spill or empty out of the container through a top opening.

The first cutout can be selected from multiple shapes, such as a half cylinder of various diameters or wine glass shape. The first cutout is preferably present on an outermost edge of the end of the forearm support that is near the digits of the wearer's hand present in the sling. It is noted that this could be either end of the forearm support in order to accommodate the left or right arm/hand of the wearer, but should be placed near the digits of the wearer's hand which is present in the sling.

A second cutout of a different shape than the first cutout can be present adjacent the first cutout on the end of the forearm support.

In an alternate embodiment, the second cutout is the same as the first cutout.

The forearm support can additionally contain at least one additional cavity or hole along the top surface of the forearm support, a length from the first and/or second cutout on the outermost edge of the end of the forearm support for maintaining a beverage container upright.

The first cutout and/or second cutout can be insulated with an additional material present in the cutout and different than the material of the forearm support. The additional material can provide a surface with which the beverage interacts instead of the material of the forearm support in which the cutout is made, in order to reduce wear within the one or more cutouts. The additional cavity or hole along the top surface of the forearm support can optionally include an insulation material or other covering which protects the cushion material of the forearm support from wear. The insulation material or covering used in the additional cavity or hole or the first/second cutouts can be removed for washing or replacement.

BRIEF DESCRIPTION OF THE DRAWINGS

FIG. 2 shows an end view of the forearm support with a single cutout.

FIG. 3 shows an end view of the forearm support with two cutouts of different lengths.

FIG. 4 shows an end view of the forearm support with two cutouts for different shaped containers.

FIG. 5 shows an end view of the forearm support with two different cutouts to accommodate various sized containers within a single cutout.

FIG. 6 shows an end view of the forearm support with a cutout accommodating the bowl, stem and foot of a wine glass.

FIG. 7 shows an example of a wine glass.

FIG. 8 shows an example of a can.

DETAILED DESCRIPTION

Figure 1:
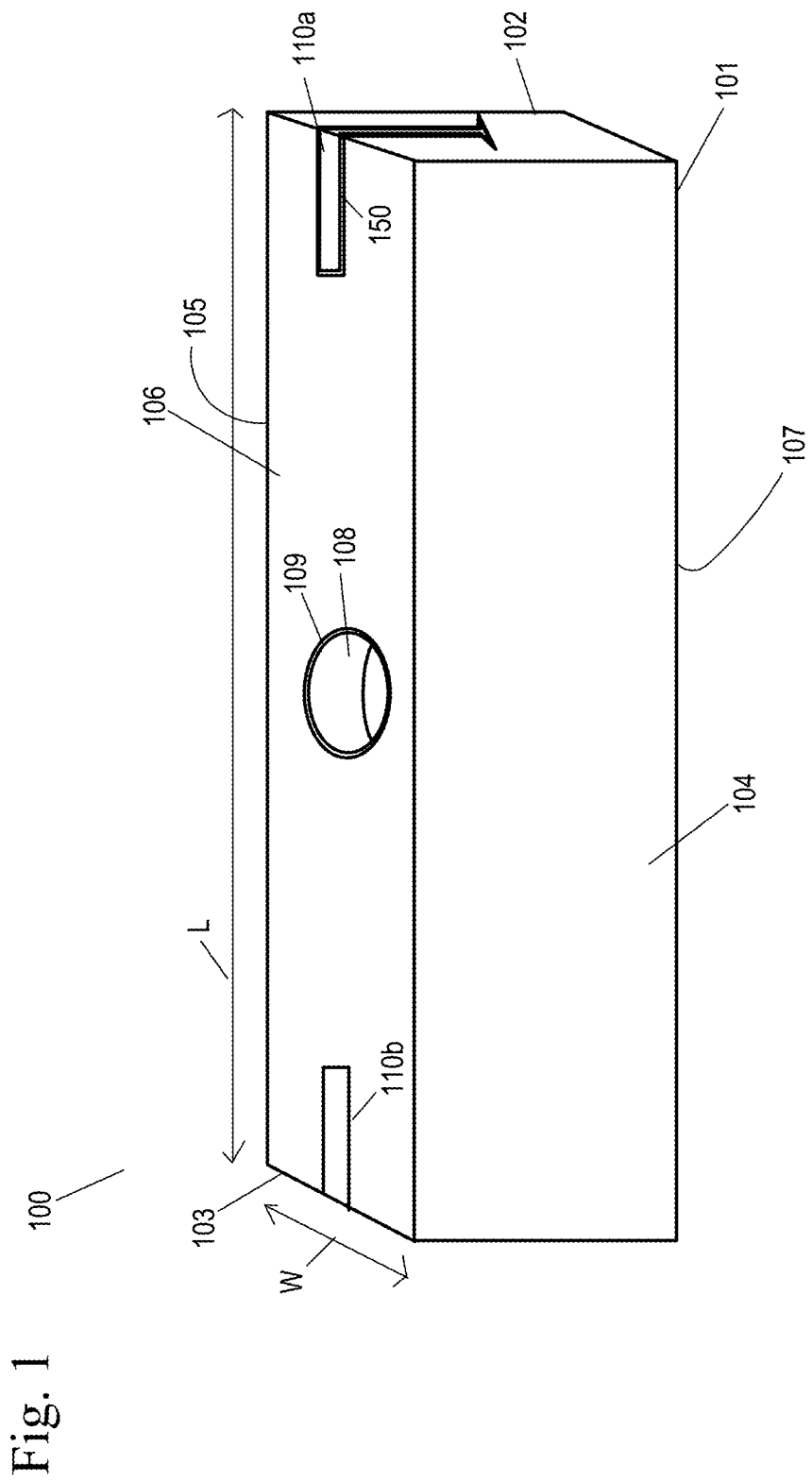
FIG. 1 shows a schematic of a forearm support with a cutout and an additional cavity.

FIG. 1 shows a schematic of the forearm support for use by a wearer with a sling (not shown). It is noted that straps and means of attachments for securing the forearm support to the wearer or in a specific position are not shown for clarity purposes, but could be present on either end, adjacent a corner between the top surface and a side surface, connected to a back, a combination of surfaces, or any surface of the forearm support.

The forearm support 100 has a body 101 with first side 104, a second side 105, a first end 102, a second end 103, and a length L between the first end 102 and the second end 103, a top surface 106 and a bottom surface 107. At least one of the first end 102 or the second end 103 has a width W to accommodate at least one cutout 110*a*, 110*b* described below.

Any cutouts 110-118 present in the forearm support 100 are preferably present in the first end 102 and the second end 103. For example, FIG. 1 shows the first cutout 110*a* on the first end 102 and the same shaped cutout 110b on the second end 103. While not shown for all of the cutout shapes, it is within the scope of the invention that the cutouts present on one end can also be present on the opposite end.

The one or more cutouts 110-118 can extend from the top surface 106 of the body 101 toward the bottom surface 107 and inwards from a first end 102 towards a second end 103 or from a second end 103 towards a first end 102 as shown in FIG. 1. The cutouts 110-118 preferably have a depth to accommodate at least half of the diameter of the beverage container received. In another embodiment, the depth of the cutouts is greater than half of the of the diameter of the beverage container received. For use, the wearer would position the one or more cutouts 110-118 near or adjacent the end closest to the wearer's digits of arm in the sling or being used with the forearm support 100. By having one or more cutouts 110-118 on both the first end 102 and the second end 103, the forearm support 100 can be used by the wearer for the left arm/hand or the right arm/hand.

A first cutout 110a can be present within the first end 102 of the forearm support 100 and the same first cutout 110b can also be present within the second end 103 as shown in FIG. 1. FIGS. 2-6 and 10-12 show cutouts 110-118 present in only the first end 102, however, the same cutouts could be present on the second end 103 to accommodate either hand of the wearer. In another embodiment, the forearm support 100 can be designated for a specific hand of the wearer and the one or more cutouts 110-118 would only be present on one of the first end 102 or the second end 103.

Figure 9:
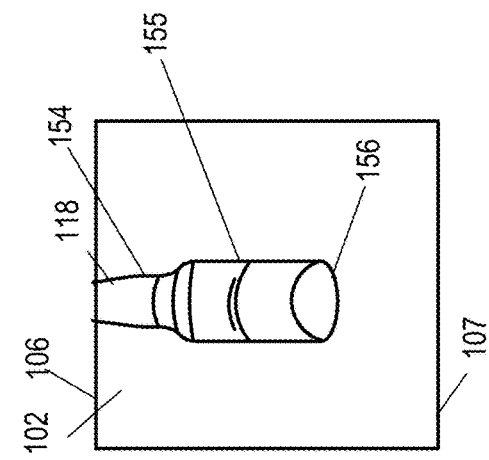
FIG. 9 shows an example of a bottle.

The cutouts 110-118 are shaped to support different shaped beverage containers, for example a wine glass 130 or similar glassware containing a stem and a foot (e.g. champagne flute, martini glass), a can 131 or similar circular shaped container, and a bottle 160. FIG. 7 shows an example of a wine glass 130 having a foot 124 connected to a bowl 122 via stem 123, with the bowl 122 having an opening with a lip 120. The cutouts 110-118 maintain the beverage containers 130, 131, 160 upright such that fluid present within the beverage containers 130, 131, 160 does not spill out of the associated openings 121, 126, 157 when in the cutouts 110-118. FIG. 8 shows an example of a can 131 having a cylindrical body 127 with a barrier top 125 having an opening 126. FIG. 9 shows an example of a bottle 160 having a base 153 connected to a neck 151 through a body 152. An opening 157 is present at the end of the neck 151.

The cutout 110, 112, 114 is shown as being shaped to accommodate at least the foot 124 and the stem 123 of a wine glass 130. Therefore, the cutout 110, 112, 114 has a triangular base 141 and a cylindrical portion 142. In these cutouts 110, 112, 114, the bowl 122 rests on the top surface 106 of the forearm support 100 when the foot 124 and the stem 123 are received within the triangular base 141, 146, 147, 148, 149 and the cylindrical portion 142, 143 of the cutout.

The cutout 116 can additionally be modified to accommodate the bowl 122 of the wine glass 130 as well, as shown in FIG. 6 in which the cutout 116 has a triangular base 141 to receive the stem 124 of the wine glass, a cylindrical portion 142 to receive the stem 123 of the wine glass 130 and a semicircular portion 144 which receives the bowl 122 of the wine glass 130. The width of the bowl 122 can vary from that shown in Figures within the scope of the invention.

A second cutout 110-118 of a different shape or size than the first cutout 110-116 can be present adjacent the first cutout on the end 102, 103 of the forearm support 100. For example, FIG. 3 shows a first cutout 110 to receive the foot 124 and stem 123 of a wine glass 130 and a second cutout 112 adjacent the first cutout 110 with a triangular base 141 to accommodate the foot 124 of the wine glass 130 and a longer cylindrical portion 143 than cylindrical portion 142 to accommodate a longer stem 143 of a wine glass 130.

Figure 13:
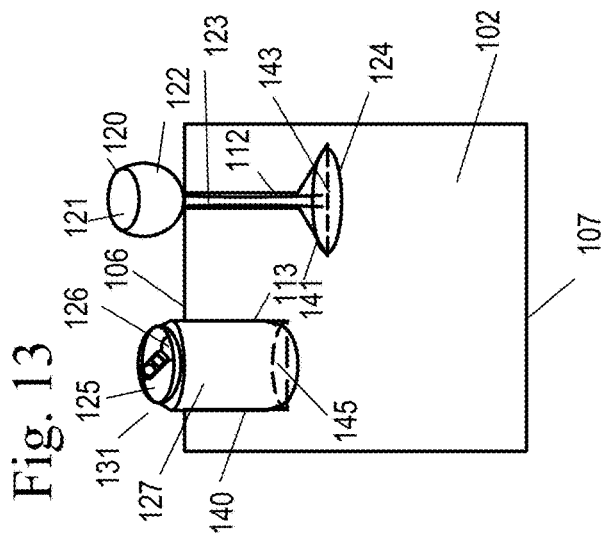
FIG. 13 shows an end view of the forearm support with two cutouts for different shaped containers including their respective beverage containers.

FIG. 4 shows another embodiment in which a first cutout 113 includes a half cylinder portion having a semicircular base 145 connected to a length 140 to receive a cylindrical shaped beverage container 131, such as, but not limited to a can, open container, water bottle, shot glass, container with a handle, and a second cutout 112 to accommodate the foot 124 and a stem 123 of a wine glass 130. The semicircular base 145 of the cutout 113 receives the cylindrical body 127 of the cylindrical shaped beverage container 131. The opening 126 is parallel to the top surface 106 of the forearm support 100 and is not present within the second cutout 112. It is noted that the bowl 122 of the wine glass 130 therefore sits on the top surface 106 of the forearm support 100 as shown in FIG. 13.

FIG. 5 shows another embodiment in which a first cutout 110 accommodates a foot 124 and stem 123 of a wine glass 130 with the bowl 122 of the wine glass 130 and a second cutout 114 which accommodates various lengths of stems 123 of wine glasses 130 and their associated foot 124 with a plurality of spaced apart triangular bases 146, 147, 148, 149 connected to a common cylindrical portion 143. Any bowl 122 of the wine glass for either the first cutout 110 or the second cutout 114 sits on the top surface 106 such that the opening 121 is parallel to the top surface 106.

FIG. 6 shows an embodiment in which only a first cutout 116 is present and accommodates the foot 124, stem 123 and a portion of the bowl 122 of the wine glass 130. The cutout 116 has a triangular base 141 to receive the stem 124 of the wine glass 130, a cylindrical portion 142 to receive the stem 123 of the wine glass 130 and a semicircular portion 144 which receives the bowl 122 of the wine glass 130.

Figure 10:
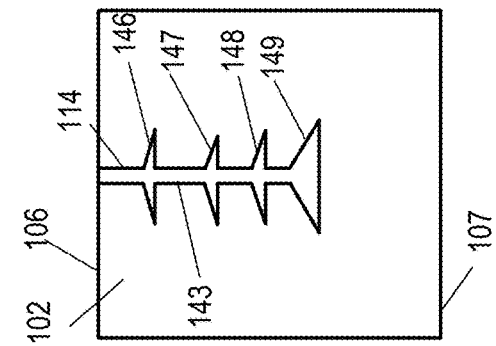
FIG. 10 shows an end view of the forearm support with a cutout of a plurality of spaced apart triangular bases.
Figure 14:
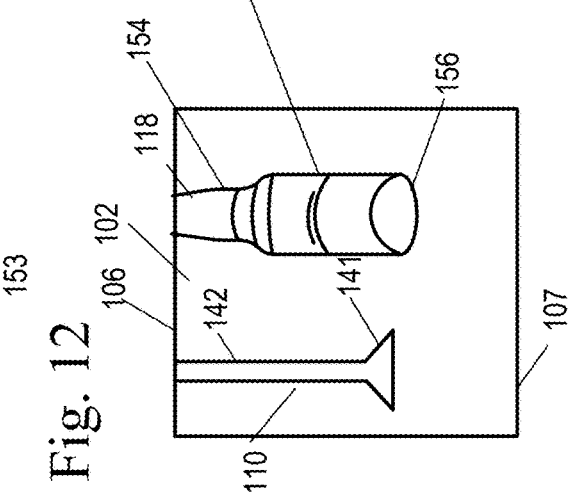
FIG. 14 shows an end view of the forearm support with two cutouts, a first cutout with a plurality of spaced apart triangular bases and a second cutout for receiving a bottle including their respective beverage containers.

FIG. 10 shows an embodiment in which only a first cutout 114 is present. The first cutout 114 accommodates various lengths of stems 123 of wine glasses 130 and their associated foot 124 with a plurality of spaced apart triangular bases 146, 147, 148, 149 connected to a common cylindrical portion 143. Therefore, this cutout can accommodate many different types of glassware, with the foot 124 being placed in the appropriate triangular base 146, 147, 148, 149 that allows the bowl 122 of the wine glass 130 to seat adjacent the top surface 106 of the forearm support. FIG. 14 shows a wine glass 130 present within the cutout 114.

Figure 11:
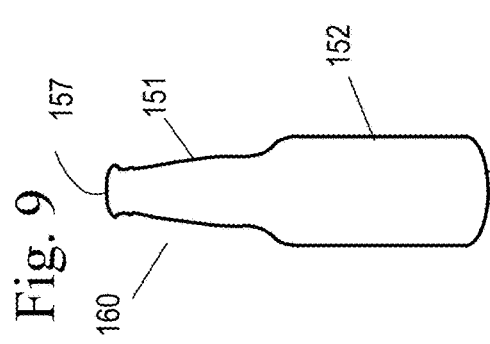
FIG. 11 shows an end view of the forearm support with a cutout for a bottle.

FIG. 11 shows an embodiment in which only a first cutout 118 is present and accommodates a body 152 of the bottle 160 with the narrow portion 154 of the cutout 118 receiving the neck 151 of the bottle 160. In this embodiment, the opening 157 is parallel to the top surface 106 of the forearm support 100. FIG. 14 shows the bottle 160 present within the cutout 118.

Figure 12:
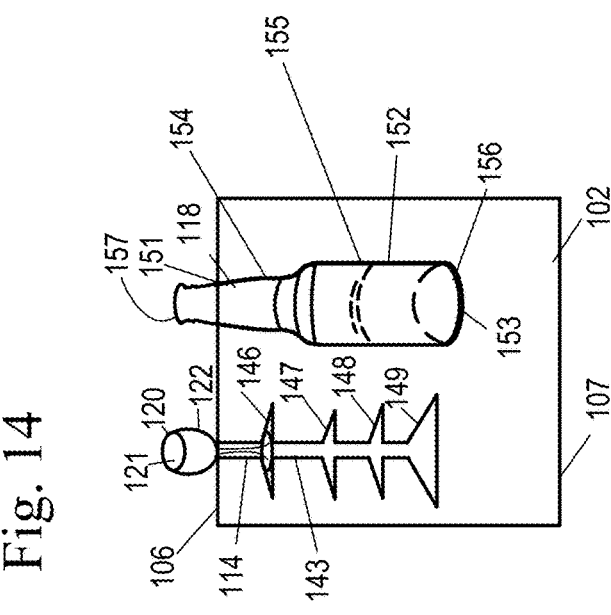
FIG. 12 shows an end view of the forearm support with a cutout accommodating a wine glass and a bottle.

FIG. 12 shows an embodiment in which the first cutout 110 accommodates a foot 124 and a stem 123 of a wine glass 130 and a second cutout 114 which accommodates a bottle 160 by receiving the base 153 of the bottle 160 in the semicircular base 156 of the cutout 118, the cylindrical body 155 of the cutout 118 receiving the body 152 of the bottle 160 and the narrow portion 154 of the cutout 118 receiving the neck 151 of the bottle 160. In this embodiment, the bowl 122 of the wine glass 130 sits on the top surface 106 of the forearm support with the opening 121 being parallel to the top surface 106 and the opening 157 of the bottle 160 is parallel to the top surface 106.

While the above embodiments show different shapes for the first cutout 110-118 and the second cutout 110-118, the first cutout 110-118 and the second cutout 110-118 may alternatively be the same. Any of the cutout shapes 110-118 discussed above can be paired with any the other cutout shapes discussed without deviating from the scope of the invention. Furthermore, any of the ends 103, 105 of the forearm support 100 can contain only a single, first cutout 110-118, for example as shown in FIG. 2, FIG. 6, FIG. 10 or FIG. 11.

While the forearm support 100 is shown as having a generally rectangular shape, other shapes are possible, as long as at least one end 102, 103 has the length associated with the first side 104 and the second side 106 and width W to accommodate at least one cutout 110-118 as described. In one embodiment, along the length L of the body 101 of the forearm support 100 and extending from the top surface 106 is a cavity or hole 108. While the cavity 108 is shown in the middle of the body 101 between the first end 102 and the second end 103, the cavity 108 can be placed anywhere along the length L of the body 101 of the top surface 106 of the forearm support 100. The cavity 108 can maintain a beverage container 130, 131 in an upright position or be used to contain other items.

It is noted that an upright position of a beverage container 130, 131, 160 is considered to be a position in which the beverage container 130, 131, 160 is generally vertical with an opening 121, 126, 157 present, at a top position, which may or may not be above the surface of the forearm support 100, such that any liquid present in the beverage container 130, 131, 160 does not escape through the opening 121, 126, 157 present at the top of the beverage container 130, 131, 160 due to movement of the wearer of the forearm support 100, when the forearm support 100 is kept generally horizontal. The openings 121, 126, 157 are preferably parallel to the top surface 106 of the forearm support 100. The opening 121, 126, 157 of the beverage container 130, 131, 160 may be partially enclosed, for example a soda can with an opening 126 at a top of the beverage container surrounded by barrier top 125 as shown in FIG. 8 or an unobstructed opening 121, 157 without any barrier between the lip 120 of the beverage container 130, 160 and the liquid present within the beverage container 130, 160 such as a glass, wine glass or bottle as shown in FIGS. 7 and 9 respectively.

The first cutout and/or second cutout 110-118 can be insulated with an additional material present 150 in the cutout 110-118 and different than the material of the forearm support, which can be a foam. The additional material 150 can provide a surface with which the beverage container 130, 131 interacts instead of the material of the forearm support in which the cutout 110-118 is made into, in order to reduce wear within the one or more cutouts 110-118. The additional material 150 can additionally provide insulation to aid in maintaining the liquid within the beverage container at a specific temperature. The additional material 150 can be removed for washing or replacement.

The additional cavity or hole 108 along the length L of the forearm support 100 within the top surface 106 can optionally include an insulation material or other covering 109 which protects the cushion material of the forearm support 100 from wear. The insulation material or covering 109 used in the additional cavity or hole 108 can be removed for washing or replacement.

It is also noted that the term "glass" as used herein does not refer to or restrict the material of the beverage container.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A forearm support for use by a wearer in addition to a sling to hold at least one beverage container, the forearm support comprising:
   a body having a first side, a second side opposite the first side, a first end, a second end, opposite the first end and separated by a length from the first end, a top surface, and a bottom surface opposite the top surface; and
   at least two cutouts at one or both of the first end and the second end, the at least two cutouts extending from the top surface towards the bottom surface and extending inward from the first end or the second end towards the body, the at least two cutouts having a depth adapted to receive the at least one beverage container, a first cutout of the at least two cutouts comprises at least two triangular bases separated by a cylindrical portion, adapted to selectively receive a base and a stem of a first beverage container of the at least one beverage container; and a second cutout of the at least two cutouts receiving a second beverage container of the at least one beverage container, the second cutout comprises a triangular base connected to a cylindrical portion.

2. The forearm support of claim 1, wherein a length of the cylindrical portion of the first cutout and the second cutout is different.

3. The forearm support of claim 1, wherein the second cutout further comprises a semicircular portion connected to an end of the cylindrical portion, such that the semicircular portion of the second cutout is adapted to receive a bowl of the second beverage container.

4. The forearm support of claim 3, wherein the second beverage container received within the second cutout is a wine glass.

5. The forearm support of claim 1, wherein the first cutout further comprises an insulating fabric.

6. The forearm support of claim 1, further comprising a cavity in the top surface of the body along the length of the body of the forearm support.

7. The forearm support of claim 6, wherein the cavity further comprises an insulating fabric.

8. The forearm support of claim 1, wherein the first beverage container is a wine glass.

9. A forearm support for use by a wearer in addition to a sling to hold at least one beverage container, the forearm support comprising:
   a body having a first side, a second side opposite the first side, a first end, a second end, opposite the first end and separated by a length from the first end, a top surface, and a bottom surface opposite the top surface; and
   at least two cutouts at one or both of the first end and the second end, the at least two cutouts extending from the top surface towards the bottom surface and extending inward from the first end or the second end towards the body, the at least two cutouts having a depth adapted to receive a first beverage container, wherein a first cutout of the at least two cutouts comprises a triangular base connected to a cylindrical portion and a second cutout of the at least two cutouts receiving a second beverage container, the second cutout comprises a semicircular base.

10. The forearm support of claim 9, wherein the second cutout further comprises a body extending a length from the semicircular base.

11. The forearm support of claim 10, wherein the first cutout is for the first beverage container of a wine glass, such that the triangular base is adapted to receive a base of the wine glass and the cylindrical portion is adapted to receive a stem of the wine glass and the second cutout is for the second beverage container of a can or glass, such that the semicircular base is adapted to receive a base of the can or glass and the body of the second cutout is adapted to receive a body of the can or glass.

12. The forearm support of claim 9, wherein the second cutout further comprises a cylindrical body connected to the semicircular base and a narrow portion extending from the cylindrical body.

13. The forearm support of claim 12, wherein the first beverage container received within the first cutout is a wine glass and the second beverage container received within the second cutout is a bottle.

14. The forearm support of claim 12, wherein the semicircular base of the second cutout is adapted to receive a base of the second beverage container, the cylindrical body of the second cutout is adapted to receive a body of the second beverage container and the narrow portion of the second cutout is adapted to receive a neck of the second beverage container.

15. The forearm support of claim 12, wherein the second beverage container is a bottle.

16. The forearm support of claim 9, wherein the second beverage container is a can or an open container.

17. The forearm support of claim 9, wherein the triangular base of the first cutout further comprises at least two triangular bases separated by the cylindrical portion.

\* \* \* \* \*